(12) United States Patent
Cockerham

(10) Patent No.: US 7,318,433 B2
(45) Date of Patent: Jan. 15, 2008

(54) GAS DELIVERY DEVICE FOR INFANTS

(76) Inventor: Daniel S. Cockerham, 8795 W. Florence Dr., Magna, UT (US) 84044

( * ) Notice: Subject to any disclaimer, the term of this patent is extended or adjusted under 35 U.S.C. 154(b) by 0 days.

(21) Appl. No.: 11/054,517

(22) Filed: Feb. 8, 2005

(65) Prior Publication Data

US 2005/0188992 A1 Sep. 1, 2005

Related U.S. Application Data

(60) Provisional application No. 60/543,093, filed on Feb. 9, 2004.

(51) Int. Cl.
*A61M 16/00* (2006.01)
*A62B 18/08* (2006.01)
*A61J 17/00* (2006.01)

(52) U.S. Cl. .......................... 128/201.26; 128/206.29; 606/234

(58) Field of Classification Search ............ 128/200.21, 128/200.26, 202.27, 203.12, 203.29, 204.18, 128/206.29, 911, 201.26; 606/234–236

See application file for complete search history.

(56) References Cited

U.S. PATENT DOCUMENTS

| 4,520,809 A | 6/1985 | de Greef et al. |
| 4,669,461 A | 6/1987 | Battaglia et al. |
| 4,896,666 A * | 1/1990 | Hinkle .................. 128/202.13 |
| 5,375,593 A | 12/1994 | Press |
| 5,462,050 A * | 10/1995 | Dahlstrand ............. 128/207.18 |
| 5,512,047 A * | 4/1996 | Dvorak ........................ 604/77 |
| 5,685,291 A | 11/1997 | Marsh |
| 5,904,140 A | 5/1999 | McGoogan |
| 6,418,929 B1 | 7/2002 | Norfleet |
| 6,470,882 B1 | 10/2002 | Newhouse et al. |
| 6,526,966 B1 | 3/2003 | Peesay |
| 6,557,548 B1 | 5/2003 | Dickson |
| 6,626,168 B1 | 9/2003 | Carroll et al. |
| 6,776,157 B2 | 8/2004 | Williams et al. |
| 6,905,507 B2 * | 6/2005 | Hinshaw ...................... 606/235 |
| 2004/0040556 A1 | 3/2004 | Fillyaw |
| 2005/0263157 A1* | 12/2005 | Olsen ..................... 128/206.28 |

* cited by examiner

*Primary Examiner*—Teena Mitchell
(74) *Attorney, Agent, or Firm*—Thorpe North & Western LLP

(57) ABSTRACT

An improved gas delivery device for infants which is simple and easy to use is disclosed and described. The gas delivery device can include a gas supply chamber and a nipple directly connected to the supply chamber. The gas supply chamber can define a substantially hollow region and can have a front portion which has the nipple connected thereto. The front portion has a plurality of holes which are designed to direct gas forward from the hollow region toward the infant. The nipple can be a substantially continuous material. Such a gas delivery device is unobtrusive, easy to use, and inexpensive to manufacture.

20 Claims, 1 Drawing Sheet

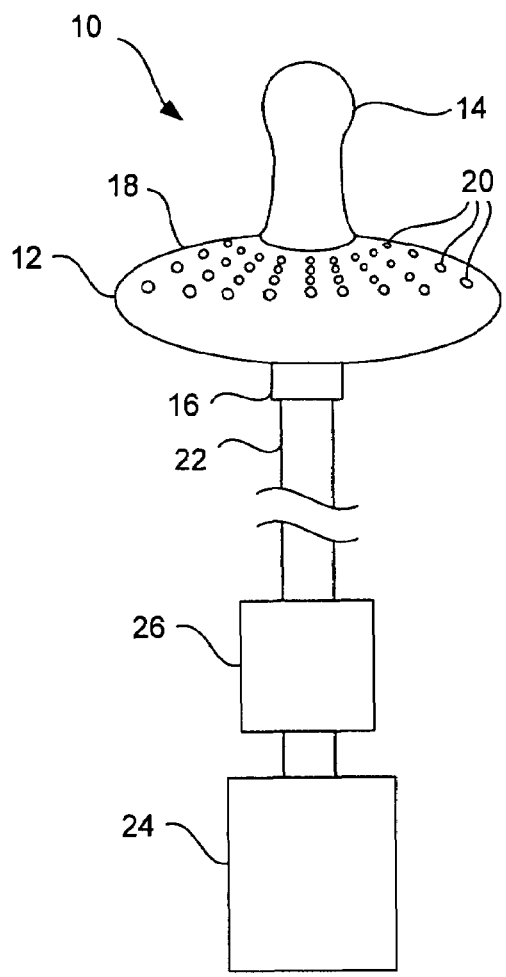
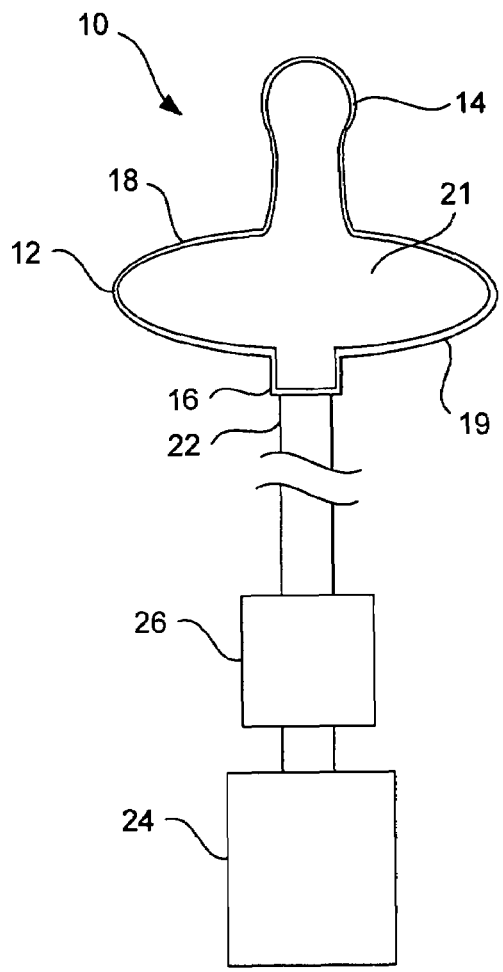
FIG. 1
FIG. 2
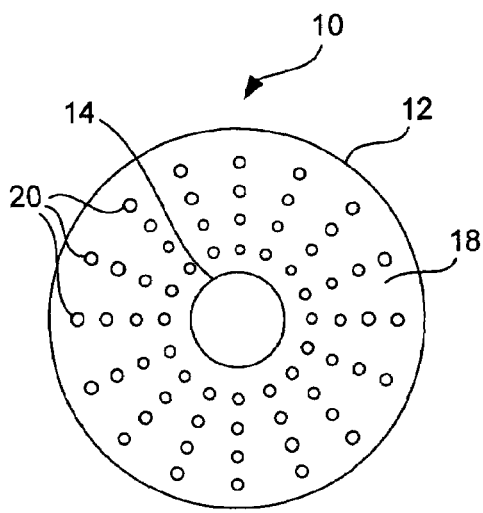
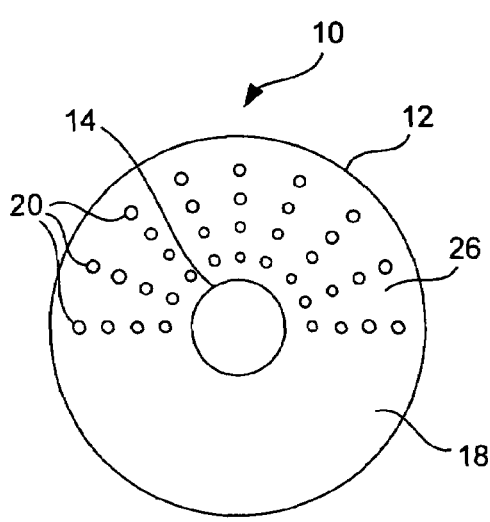
FIG. 3
FIG. 4

GAS DELIVERY DEVICE FOR INFANTS

RELATED APPLICATIONS

This application claims the priority of U.S. Provisional Application No. 60/543,093, filed Feb. 9, 2004, which is incorporated herein by reference in its entirety.

FIELD OF THE INVENTION

The present invention relates generally to medical devices used for delivery of gases. More specifically, the present invention relates to medical devices used for delivery of gases, such as oxygen, to an infant. Accordingly, the present invention involves the fields of medical devices, pediatrics, and materials science.

BACKGROUND OF THE INVENTION

During medical treatments it is often desirable to deliver oxygen and/or other gases to a patient. Oxygen can be used in treatment of respiratory distress, RSV, croup, bronchitis, or any number of other medical treatments. A wide variety of medical devices and processes for delivering gases to a patient are available. The most common device is an oxygen mask which can be held or strapped to the head of a patient. However, in the case of infants, masks are often difficult to attach or retain on the infant. For example, the infant will often become frightened or agitated by such a device sufficient that they may remove the mask or decrease the effective delivery of gas.

Various devices have attempted to compensate for this problem. However, these devices suffer from a number of defects which reduce their commercial and/or practical value. Specifically, many of these devices include a nebulizer and/or other medicine delivery members as part of the mask or immediately adjacent thereto. This can increase the weight of the device and can be an intimidating view to infants. Further, many of these devices include holes in the sucking portion which can be problematic in controlling the rate of delivery of medicine and oxygen. In addition, many of the available devices are relatively expensive to manufacture and can be difficult to use. Therefore, medical devices which avoid the above mentioned problems continue to be sought.

SUMMARY OF THE INVENTION

It has been recognized by the inventor that it would be advantageous to develop a device and method for delivering gases to infants which is simple and inexpensive to produce and use.

In one aspect, the present invention resolves the problems set forth above by providing a gas delivery device including a gas supply chamber and a nipple directly connected to the supply chamber. A gas inlet can be provided to the gas supply chamber for connection to a gas supply line and/or gas source. The gas supply chamber can define a substantially hollow region and can have a front portion. The front portion can be the surface which has the nipple connected thereto. Further, the front portion can have a plurality of holes which are configured to direct gas forward from the hollow region toward the infant. The nipple can be connected to the front portion and is a substantially continuous piece of material which is free of holes.

In general, the gas supply chamber can be similar dimensions to a standard pacifier and can be configured in a number of embodiments.

For example, in one detailed embodiment of the present invention, the gas supply chamber and nipple can be molded of a single piece of material. Alternatively, the gas supply chamber can be formed of a first material which is coupled to the nipple by any convenient means such as gluing, snapping, interference fitting, or other mechanical coupling.

In another detailed embodiment of the present invention, the gas supply chamber can be formed of a front portion and a rear portion which are coupled together to form the gas supply chamber. Preferably, the gas supply chamber is permanently enclosed such that the hollow region is not accessible. This is particularly important in reducing the complexity of the device and manufacturing steps required. Further, as the device can be designed as a single-use item, cleaning and maintenance is not required and is preferably avoided.

In yet another detailed embodiment of the present invention, the front portion has a surface contour which is convex, concave, or flat. Each surface contour can be desirable for a particular circumstance. For example, a convex surface contour is currently a preferred configuration. The convex surface contour allows most of the holes to be unobstructed during administration of the gas. Further, the convex shape can more closely approximate nipples found in bottles and natural breast feeding.

In another aspect of the present invention, a number of gases can be delivered using the medical device described herein. Those skilled in the art will recognize the particular gases which are appropriate for a specific treatment. Non-limiting examples of gases which can be used in connection with the present invention include oxygen, nitrous oxide, normal saline, Atrovent® (ipratropium bromide), Combivent® (ipratropium bromide and albuterol sulfate), racemic epi (epinephrine), albuterol, and mixtures thereof. Currently, it is anticipated that the dominant gas which will be used is oxygen. These gas treatments can be used in connection with treatment of a wide variety of ailments including, but certainly not limited to, respiratory distress associated with RSV, croup, bronchitis, underdeveloped lungs, asthma, or the like.

In yet another aspect of the present invention, the gas delivery device can be conveniently configured as a single-use item. This helps to reduce or eliminate the amount of time and effort required to clean and/or maintain the device from patient-to-patient. Rather, the simple use and low-cost manufacturing can allow medical care providers to dispose of the device after a single use or after a specific patient. This is often not an option with other similar devices which are more expensive and complex.

In an additional aspect of the present invention, the nipple can be formed of a wide variety of materials. Suitable materials can include, but are in no way limited to, polymeric materials such as latex resins, polyacrylate resins, rubbers, and the like.

Typically, the nipple can be formed as a flexible hollow member that is sufficiently durable to withstand treatment of at least a single patient. In most cases, it can be desirable to form the nipple and device of materials which are sufficiently durable for use over at least a few days by the same patient.

In another detailed aspect of the present invention, the gas delivery device can include only a nipple connected to a gas supply chamber which defines a hollow region. In this preferred embodiment, the gas supply chamber can includes only an inlet and a plurality of holes such that the front and back portions are substantially free of any external baffles, internal baffles, lips, ridges, or other similar members. FIGS.

1 and 2 illustrate one configuration of this embodiment. The interior hollow region can be characterized by a substantially open volume which conforms to the exterior shape of the gas supply chamber.

In an additional aspect of the present invention, the front portion can be configured such that the plurality of holes are substantially all directed toward the infant. In this manner, exiting gas is delivered toward the infant. Thus, in some embodiments the plurality of holes can be placed around the full face of the front portion. As a result, the position and orientation of the gas delivery device does not affect performance. Alternatively, the plurality of holes can be concentrated at an upper region of the front portion which is designed to be nearer the nose of the infant. For example, the inlet can include an elbow portion which bends downward or in an opposite direction than the upper region. Optionally, the elbow portion can be adjustable to orient the position of the upper portion closer to the nose of the infant. In any of the above embodiments, the configuration of the plurality of holes to direct gas toward the infant helps to avoid waste of the gas which can occur during administration using devices which have either peripheral openings or include deflection and baffling features.

In yet another aspect of the present invention, a gas tube can be operatively connected to the gas inlet. The gas tube can have any length which is functional. Of particular consideration is providing a nebulizer which is upstream the gas inlet. Placing the nebulizer farther upstream can allow for fewer obstructions around the infant and less intimidation of the infant during use. For example, a gas tube having a length from about 2 feet to about 10 feet can allow for increased comfort, improved access to the infant, and convenient operation of the device.

Another aspect of the present invention can include a method utilizing the above described devices. Specifically, the method can include administering gas to an infant using a gas delivery device as described above. The nipple can be oriented and/or placed in the mouth of the infant. A gas can be supplied to the inlet portion at a sufficient pressure to deliver the gas through the plurality of holes. Of course, the gas delivery line can be attached before or after the device is placed on the infant. Similarly, the gas supply source can be turned on either before or after orientation of the gas delivery device.

In a detailed aspect of the present invention, the gas supply source can provide the gas at a pressure from about 0.5 liters/minute to about 15 liters/minute.

There has thus been outlined various features of the invention so that the detailed description thereof that follows may be better understood, and so that the present contribution to the art may be better appreciated. Other features of the present invention will become more clear from the following detailed description of the invention, taken with the accompanying drawings and claims, or may be learned by the practice of the invention.

BRIEF DESCRIPTION OF THE DRAWINGS

FIG. 1 is a side perspective view of a gas delivery device in accordance with one embodiment of the present invention.

FIG. 2 is a side cross-sectional view of FIG. 1 in accordance with one embodiment of the present invention.

FIG. 3 is a top view of the device shown in FIG. 1.

FIG. 4 is a top view of a gas delivery device having a pattern of holes in accordance with another embodiment of the present invention.

The figures herein are provided merely for illustrative purposes and dimensions and relative proportions are not always to scale and may deviate from those illustrated.

DETAILED DESCRIPTION

Reference will now be made to exemplary embodiments and specific language will be used herein to describe the same. It will nevertheless be understood that no limitation of the scope of the invention is thereby intended. Alterations and further modifications of the inventive features, process steps, and materials illustrated herein, and additional applications of the principles of the inventions as illustrated herein, which would occur to one skilled in the relevant art and having possession of this disclosure, are to be considered within the scope of the invention. It should also be understood that terminology employed herein is used for the purpose of describing particular embodiments only and is not intended to be limiting.

A. Definitions

In describing and claiming the present invention, the following terminology will be used.

The singular forms "a," "an," and "the" include plural referents unless the context clearly dictates otherwise. Thus, for example, reference to "a hole" includes reference to one or more of such holes, and reference to "an inlet" includes reference to one or more of such features, and reference to "supplying a gas" includes reference to supplying one or more steps of supplying the same or difference gases.

As used herein, "infant" refers to neonatal or pediatric patients. Infants can also include children for whom a pacifier is comforting and useful for delivering gases in a non-threatening circumstance.

As used herein, "substantially continuous" refers to a surface or material which is free of discontinuous features such as apertures, holes, slits, or the like.

As used herein, "fluid communication" refers to the ability of a fluid to flow freely and unobstructed among the identified features.

As used herein, "enclosed nipple" refers to a nipple having no apertures or openings. An enclosed nipple does not allow gas or other material to exit the hollow region into the mouth of an infant.

As used herein, "permanently enclosed" is intended to mean that the gas supply chamber is enclosed and not accessible without substantial destruction of the device.

As used herein, "baffles" refer to any wall, member, or feature which is placed to direct flow of a fluid either on an exterior or interior surface of the device. Most embodiments of the present invention are designed for their simplicity and do not include baffles.

As used herein, "single-use" refers to a property of a device or material which renders it useful for an intended purpose for a limited period of time. Specifically, a single-use medical device is designed to function without cleaning or maintenance during treatment of a single patient for a specified treatment, e.g., two to three days.

As used herein, "region" refers to an area of material which can be characterized by dimensions, features, or other relevant properties.

As used herein, "predetermined pattern" refers to a non-random pattern that is identified prior to formation of a front portion. Further, such patterns are not limited to uniform grid or radially extending lines but may include any number of configurations based on the desired gas flow.

As used herein with respect to an identified property or circumstance, "substantially" refers to a degree of deviation that is sufficiently small so as to not measurably detract from the identified property or circumstance. The exact degree of deviation allowable may in some cases depend on the specific context. Thus, for example, a front surface which has a "substantially flat" surface contour may deviate from exactly level across the entire surface by margins which are within standard manufacturing limits.

As used herein, "substantially free of" or the like refers to the lack of an identified element or agent. Particularly, elements that are identified as being "substantially free of" are either completely absent, or are included only in amounts which are small enough so as to have no measurable effect on the device performance.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

B. The Invention

It is to be understood that the following description is only exemplary of the principles of the present invention, and should not be viewed as narrowing the appended claims.

Referring now to FIG. 1, a gas delivery device is shown generally at 10. The gas delivery device can generally include a gas supply chamber 12 and a nipple 14 directly connected to the supply chamber. The gas supply chamber can define a substantially hollow region and can have a front portion 18.

In general, the gas supply chamber can be configured in a number of embodiments. The size and the shape of the gas supply chamber can be varied. In one embodiment, the gas supply chamber can be of a size which is similar to that of a standard pacifier. Dimensions from about 4 cm to about 6 cm in diameter are typical although other sizes can be useful.

Optionally, the gas supply chamber 12 and nipple 14 can be molded of a single piece of material. Forming the supply chamber and nipple of a single material can also reduce the possibility that the nipple will become detached from the supply chamber. Alternatively, the gas supply chamber can be formed of a first material which is coupled to the nipple by any convenient means such as gluing, snapping, interference fitting, or other mechanical coupling.

In yet another alternative, the gas supply chamber can be formed of a front portion 18 and a rear portion 19 which are coupled together to form the gas supply chamber. Preferably, the gas supply chamber is permanently enclosed such that the hollow region is not accessible. This is particularly important in reducing the complexity of the device and manufacturing steps required. Further, as the device can preferably be a single-use item, cleaning and maintenance is not required and can be avoided by a permanently enclosed configuration.

FIG. 2 shows a cross-section of one embodiment of the present invention. The front portion 18 and rear portion 19 form the gas supply chamber 12 and define the hollow region 21 on the interior of the device. Preferably this hollow region is substantially free space having no additional features or members therein.

The front portion 18 can be the surface which has the nipple 14 connected thereto. The front portion can have a plurality of holes 20 which are configured to direct gas forward from the hollow region toward the infant. The holes are placed in the front portion such that gas is directly delivered toward the face of an infant without the use of baffles or other members which redirect gas flow. Avoiding the use of baffles or other flow directing members can help to simplify manufacture of the device and to reduce the weight thereof. As a result, the lighter weight pacifier will more closely approximate the feel of a regular pacifier. This results in the infant typically being more cooperative and less agitated during administration of the gas.

In addition, the front portion can be configured such that the holes are substantially all directed toward the infant. In this manner, exiting gas is delivered toward the infant and is not wasted. Thus, a predetermined pattern of holes can be designed to maximize exposure of the infant to the gas. In some embodiments, such as the one shown in FIG. 3, the plurality of holes can be placed around the full surface of the front portion 18. As a result, the position and orientation of the gas delivery device does not affect performance. Alternatively, the plurality of holes 20 can be concentrated at an upper region 26 of the front portion which is designed to be nearer the nose of the infant, as illustrated in FIG. 4.

Further, the inlet 16 can include an elbow portion which bends downward or in an opposite direction than the upper region. Optionally, the elbow portion can be adjustable to orient the position of the upper portion closer to the nose of the infant. In any of the above embodiments, the configuration of the plurality of holes to direct gas toward the infant helps to avoid waste of the gas which can occur during administration using devices which have either peripheral openings or include deflection and baffling features.

Typically, the holes can be sufficiently small to prevent foreign material from entering the apertures. As a general guideline, the plurality of holes can each have a diameter which is from about 0.2 mm to about 4 mm, and preferably from about 0.5 mm to about 2 mm.

The nipple 14 can be connected to the front portion 18 and can be a substantially continuous piece of material which is free of holes. The nipple can be formed of a wide variety of materials which are suitable for oral use and provide sufficient durability. Suitable materials can include, but are in no way limited to, polymeric materials such as latex resins, silicone resins, polyvinyl chloride resins, polyacrylate resins, rubbers, and the like.

Typically, the nipple can be formed as a flexible hollow member that is sufficiently durable to withstand treatment of one or more patients. In most cases, it can be desirable to form the nipple and device of materials which are sufficiently durable for use over at least a few days by the same patient.

As mentioned above, the gas supply chamber 12 can be configured in a variety of shapes and sizes. One important aspect of the gas supply chamber is the surface contours of the front portion 18 which faces the infant's mouth during use. The front portion has a surface contour which is convex, concave, or flat. Each surface contour can be desirable for a particular circumstance. For example, a convex surface contour is currently a preferred configuration. The convex surface contour allows most of the holes to be unobstructed during administration of the gas. Further, the convex shape can more closely approximate nipples found in bottles and natural breast feeding. In general, the convex surface contour can angle from about 10° to about 30° from flat.

In another aspect of the present invention, the gas delivery device can include only a nipple connected to a gas supply chamber which defines a hollow region. In this preferred embodiment, the gas supply chamber can include only an inlet and a plurality of holes such that the front and back portions are substantially free of any external baffles, internal baffles, lips, ridges, or other similar members. FIGS. 1 and 2 illustrate one configuration of this embodiment. The interior hollow region can be characterized by a substantially open volume which conforms to the exterior shape of the gas supply chamber.

The gas inlet 16 can be provided to the gas supply chamber 12 for connection to a gas supply line 22 and/or gas source 24. The gas supply line can be any medically acceptable tubing or other gas delivery line. The gas source can supply any number of gases using the medical device described herein. Those skilled in the art will recognize the particular gases which are appropriate for a specific treatment. Non-limiting examples of gases which can be used in connection with the present invention include oxygen, nitrous oxide, normal saline, butyral Atrovent® (ipratropium bromide), Combivent® (ipratropium bromide and albuterol sulfate), racemic epi (epinephrine), albuterol, and mixtures thereof. Currently, it is anticipated that the dominant gas which will be used is oxygen. These gas treatments can be used in connection with treatment of a wide variety of ailments including, but certainly not limited to, respiratory distress associated with RSV, croup, bronchitis, underdeveloped lungs, asthma, or the like.

Beneficially, the gas delivery device of the present invention can be conveniently configured as a single-use item. This helps to reduce or eliminate the amount of time and effort required to clean and/or maintain the device from patient-to-patient. Rather, the simple use and low-cost manufacturing can allow medical care providers to dispose of the device after a single use or after a specific patient. This is often not an option with other similar devices which are more expensive and complex.

Additionally, as shown in FIG. 1, a gas tube 22 can be operatively connected to the gas inlet 16. The gas tube can have any length which is functional. Of particular consideration is providing a nebulizer 26, which is upstream the gas inlet. Placing the nebulizer substantially upstream can allow for fewer obstructions around the infant and less intimidation of the infant during use. For example, a gas tube having a length from about 2 feet to about 10 feet can allow for increased comfort, improved access to the infant, and convenient operation of the device.

Another aspect of the present invention can include a method utilizing the above described devices. Specifically, a method of administering gas to an infant can include providing a gas delivery device as described above. The nipple can be oriented and/or placed in a mouth of the infant. A gas can be supplied to the inlet portion at a sufficient pressure to deliver the gas through the plurality of holes. The gas delivery line can be attached before or after the device is placed on the infant. Similarly, the gas supply source can be turned on either before or after orientation of the gas delivery device. The gas delivery devices of the present invention can be useful for emergency medical services, hospitals, clinics, and home care in providing blow-by oxygen or other gases to a patient.

The gas supply source can be configured to supply the gas at a rate which is desirable for a given treatment. Typically, the gas supply source can provide the gas at a pressure from about 0.5 liters/minute to about 15 liters/minute. In addition, the gas supply source can include a single gas or can supply a mixture of gases and/or vaporized compounds. For example, a mixture of compounds can be pre-prepared and administered using a single tank. Alternatively, two or more gas sources can be combined through a tube coupling member and the relative pressures adjusted to control the concentrations of each compound in the mixture.

Thus, there are disclosed improved devices and methods for delivering various gases to an infant with decreased costs and improved administration. The above description and examples are intended only to illustrate certain potential embodiments of this invention. It will be readily understood by those skilled in the art that the present invention is subject to a broad range of utility and applications. Many embodiments and adaptations of the present invention other than those herein described, as well as many variations, modifications and equivalent arrangements will be apparent from or reasonably suggested by the present invention and the foregoing description thereof without departing from the substance or scope of the present invention. Accordingly, while the present invention has been described herein in detail in relation to its preferred embodiment, it is to be understood that this disclosure is only illustrative and exemplary of the present invention and is made merely for purpose of providing a full and enabling disclosure of the invention. The foregoing disclosure is not intended or to be construed to limit the present invention or otherwise to exclude any such other embodiment, adaptations, variations, modifications and equivalent arrangements, the present invention being limited only by the claims appended hereto and the equivalents thereof.

What is claimed is:

1. A gas delivery device for infants, comprising:
   a) a gas supply chamber having a gas inlet, said gas supply chamber defining a substantially enclosed hollow region in fluid communication with said gas inlet, the gas supply chamber having a front portion with a plurality of holes configured to direct gas forward from the hollow region toward the infant and a rear portion into which said gas inlet is secured to form the enclosed hollow region; and
   b) an enclosed nipple operatively connected to the front portion.

2. The gas delivery device of claim 1, wherein the gas supply chamber and nipple is molded of a single piece of material.

3. The gas delivery device of claim 1, wherein the gas supply chamber is permanently enclosed.

4. The gas delivery device of claim 1, wherein the front portion has a surface contour which is convex, concave, or flat.

5. The gas delivery device of claim 4, wherein the surface contour is convex.

6. The gas delivery device of claim 1, wherein the gas is oxygen.

7. The gas delivery device of claim 1, wherein the device is a single-use item.

8. The gas delivery device of claim 1, wherein the nipple is formed of a polymeric material.

9. The gas delivery device of claim 1, wherein the nipple is hollow.

10. The gas delivery device of claim 1, wherein the gas supply chamber is substantially free of baffles interior or exterior surfaces of the supply chamber.

11. The gas delivery device of claim 1, wherein the plurality of holes are substantially all directed toward the infant.

12. The gas delivery device of claim 1, further comprising a gas tube operatively connected to the gas inlet and a nebulizer which is upstream the gas inlet.

13. The gas delivery device of claim 12, wherein the gas tube has a length from about 2 feet to about 10 feet.

14. A gas delivery device for infants, consisting essentially of:
   a) a gas supply chamber having a gas inlet, said gas supply chamber defining a substantially enclosed hollow region in fluid communication with said gas inlet, the gas supply chamber having a front portion with a plurality of holes configured to direct gas forward from the hollow region toward the infant and a contiguous rear portion into which said gas inlet is secured to form the enclosed hollow region and wherein the gas supply chamber is permanently enclosed; and
   b) an enclosed nipple operatively connected to the front portion, said nipple being hollow.

15. A method of administering gas to an infant, comprising the steps of:
   a) providing a gas delivery device including:
      i) a gas supply chamber having a gas inlet, said gas supply chamber defining a substantially enclosed hollow region in fluid communication with said gas inlet, the gas supply chamber having a front portion with a plurality of holes configured to direct gas forward from the hollow region toward the infant and a contiguous rear portion into which said gas inlet is secured to form the enclosed hollow region; and
      ii) an enclosed nipple operatively connected to the front portion;
   b) placing the nipple in a mouth of the infant; and
   c) supplying a gas to the inlet portion at a sufficient pressure to deliver the gas through the plurality of holes.

16. The method of claim 15, wherein the gas supply chamber and nipple is molded of a single piece of material.

17. The method of claim 15, wherein the front portion has a surface contour which is convex, concave, or flat.

18. The method of claim 15, wherein the device is a single-use item.

19. The method of claim 15, further comprising a gas tube operatively connected to the gas inlet and a nebulizer which is upstream the gas inlet and configured to supply the gas.

20. The method of claim 15, wherein the pressure is from about 0.5 liters/minute to about 15 liters/minute.

* * * * *